US011266583B2

(12) United States Patent
Arnaud et al.

(10) Patent No.: US 11,266,583 B2
(45) Date of Patent: *Mar. 8, 2022

(54) COSMETIC METHOD FOR TREATING HUMAN PERSPIRATION USING PARTICLES OF AN EXPANDED AMORPHOUS MINERAL MATERIAL; COMPOSITIONS

(71) Applicant: L'OREAL, Paris (FR)

(72) Inventors: Laurence Arnaud, L'hay les Roses (FR); Delphine Ribery, Luynes (FR); Matthieu Cassier, Saint Cloud (FR); Xavier Jalenques, Gennevilliers (FR); Jean-Louis Refregier; Odile Aubrun, Antony (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/093,954

(22) Filed: Dec. 2, 2013

(65) Prior Publication Data

US 2014/0193470 A1 Jul. 10, 2014

Related U.S. Application Data

(63) Continuation of application No. 13/129,459, filed as application No. PCT/EP2009/063908 on Oct. 22, 2009, now abandoned.

(60) Provisional application No. 61/116,704, filed on Nov. 21, 2008, provisional application No. 61/116,781, filed on Nov. 21, 2008, provisional application No. 61/116,702, filed on Nov. 21, 2008.

(30) Foreign Application Priority Data

| Nov. 17, 2008 | (FR) | 0857784 |
| Nov. 17, 2008 | (FR) | 0857787 |
| Nov. 17, 2008 | (FR) | 0857788 |

(51) Int. Cl.

| *A61K 8/19* | (2006.01) |
| *A61K 8/02* | (2006.01) |
| *A61Q 15/00* | (2006.01) |
| *A61K 8/28* | (2006.01) |
| *A61K 8/25* | (2006.01) |
| *A61K 8/26* | (2006.01) |
| *A61K 8/96* | (2006.01) |

(52) U.S. Cl.
CPC .............. *A61K 8/19* (2013.01); *A61K 8/0229* (2013.01); *A61K 8/0241* (2013.01); *A61K 8/25* (2013.01); *A61K 8/26* (2013.01); *A61K 8/28* (2013.01); *A61K 8/965* (2013.01); *A61Q 15/00* (2013.01); *A61K 2800/31* (2013.01)

(58) Field of Classification Search
CPC ... A61K 8/25; A61K 8/26; A61K 8/19; A61Q 15/00

USPC ................ 424/401, 489, 65; 512/1
See application file for complete search history.

(56) References Cited

U.S. PATENT DOCUMENTS

| 1,936,845 | A | | 11/1933 | Lautmann | |
| 2,314,959 | A | * | 3/1943 | Wehe | A47K 5/10 |
| | | | | | 222/181.2 |
| 2,778,774 | A | | 1/1957 | Buslik | |
| 3,201,099 | A | | 8/1965 | Carpenter | |
| 4,450,151 | A | | 5/1984 | Shinozawa | |
| 4,524,062 | A | | 6/1985 | Laba et al. | |
| 4,786,369 | A | | 11/1988 | Kanfer et al. | |
| 5,206,019 | A | * | 4/1993 | Nichols | 424/401 |
| 5,421,291 | A | | 6/1995 | Lawson et al. | |
| 5,463,098 | A | * | 10/1995 | Giovanniello | A61K 8/0229 |
| | | | | | 424/66 |
| 5,879,414 | A | | 3/1999 | Milazzo | |
| 6,316,524 | B1 | | 11/2001 | Corzani et al. | |
| 2002/0031534 | A1 | * | 3/2002 | Horino | A61K 8/24 |
| | | | | | 424/401 |
| 2003/0044442 | A1 | * | 3/2003 | Stanier | A61K 8/0225 |
| | | | | | 424/401 |

(Continued)

FOREIGN PATENT DOCUMENTS

| CN | 1188641 A | | 7/1998 | |
| DE | 1289600 | * | 2/1969 | ............... A61K 8/25 |

(Continued)

OTHER PUBLICATIONS

English Machine Translation of DE 1289600 provided by espacenet.com on Aug. 24, 2015.*

(Continued)

*Primary Examiner* — Dominic Lazaro
(74) *Attorney, Agent, or Firm* — Polsinelli PC

(57) ABSTRACT

Provided is a cosmetic method for treating perspiration and, optionally, the body odors related to thereto, e.g. underarm odors, with an effective amount of particles of an expanded amorphous mineral material or of a composition thereof, and more particularly containing expanded perlite particles. The composition can contain, in a cosmetically acceptable carrier, at least the above particles and at least one antiperspirant salt or complex. Also provided is a composition containing, in a cosmetically acceptable carrier, at least the above particles and at least one antiperspirant salt or complex. Also, provided is an anhydrous solid composition in stick form comprising in a cosmetically acceptable carrier: (i) more than 1% by weight, relative to the total weight of the composition, of expanded mineral particles as defined above; and (ii) at least one fatty phase comprising at least one volatile oil and/or at least one non-volatile oil and a structuring agent.

20 Claims, No Drawings

(56) References Cited

U.S. PATENT DOCUMENTS

| | | | |
|---|---|---|---|
| 2003/0149157 A1 | 8/2003 | Tomlinson et al. | |
| 2004/0111810 A1 | 6/2004 | Kaizuka | |
| 2005/0163737 A1* | 7/2005 | Lemoine | A61K 8/4913 |
| | | | 424/66 |
| 2005/0175577 A1* | 8/2005 | Jenkins | A01K 1/0152 |
| | | | 424/76.1 |
| 2005/0180935 A1 | 8/2005 | Lemoine et al. | |
| 2006/0075930 A1* | 4/2006 | Wang | C04B 14/18 |
| | | | 106/638 |
| 2006/0115441 A1 | 6/2006 | James et al. | |
| 2007/0207113 A1 | 9/2007 | Joerger et al. | |
| 2010/0260866 A1* | 10/2010 | Lu | A01N 25/08 |
| | | | 424/618 |

FOREIGN PATENT DOCUMENTS

| | | | |
|---|---|---|---|
| EP | 1736138 A1 | 12/2006 | |
| FR | 2881643 A1 | 8/2006 | |
| GB | 1057316 A | 2/1967 | |
| GB | 2341866 A | 11/1999 | |
| GB | 2417683 * | 3/2006 | A61K 8/06 |
| JP | 55148560 A | 11/1980 | |
| WO | WO 03/105790 A1 | 12/2003 | |
| WO | WO 2004018606 A1 | 3/2004 | |
| WO | WO 2009/007248 A1 | 1/2009 | |

OTHER PUBLICATIONS

Perlite and It's [sic] Uses; Accessed Jan. 22, 2013; pp. 1-2; on IDS.*
Database WPI—Section Ch, Week 19814, Thomson Scientific, London, BG; Class D22, AN 1981-04752D XP002537399 "Deodorant with high active at normal temp.—comprises hydrated glyoxal and expanded vermiculite in powder, paste or slurry form etc." & JP 55 148560A (Chisso Corp) Nov. 19, 1980.
Pennsylvania Perlite Corporation (Accessed Jan. 22, 2013; pp. 1-2).
Herskovitch et al., "Upgrading of Raw Perlite by a Dry Magnetic Technique", Magnetic and Electrical Separation, 1996, vol. 7, pp. 145-161.
Printout of the internet page http://www.perlite.org./perlite_info/guides/pcf/5.pdf.

* cited by examiner

COSMETIC METHOD FOR TREATING HUMAN PERSPIRATION USING PARTICLES OF AN EXPANDED AMORPHOUS MINERAL MATERIAL; COMPOSITIONS

CROSS REFERENCE TO RELATED APPLICATIONS

This application is a Continuation of co-pending application Ser. No. 13/129,459, filed Sep. 22, 2011, which is a National Phase filing under 35 U.S.C. § 371 of PCT/EP2009/063908 filed on Oct. 22, 2009; and this application claims priority to Application No. 0857788 filed in France on Nov. 17, 2008, Application No. 0857784 filed in France on Nov. 17, 2008, and Application No. 0857787 filed in France on Nov. 17, 2008 under 35 U.S.C. § 119; and claims the benefit of U.S. Provisional Application No. 61/116,702 filed Nov. 21, 2008, U.S. Provisional Application No. 61/116,781 filed Nov. 21, 2008, and U.S. Provisional Application No. 61/116,704 filed Nov. 21, 2008; the entire contents of all are hereby incorporated by reference.

The invention relates to a cosmetic method for treating perspiration and, optionally, body odours related to human perspiration, in particular underarm odours, an effective amount of particles of an expanded amorphous mineral material or of a composition containing said particles, and more particularly of expanded perlite particles.

In the cosmetics field, it is well known to use, in topical application, antiperspirant products containing substances that have the effect of limiting or even suppressing the flow of sweat. These products are generally available in the form of roll-ons, sticks, aerosols or sprays.

Metal salts of this type are effective as an antiperspirant active agent, but some individuals find that the application of such products leads to skin irritation. Furthermore, aluminium salts block a part of perspiration by forming a partial plug in the sweat duct, which gives the consumer the impression of an unnatural perspiration control. In addition, they have a tendency to leave traces on clothing.

With the aim of obtaining a more natural control of perspiration, it has already been proposed to limit the feeling of wetness during the day by using perspiration-absorbing inorganic or organic fillers.

In patent GB 1485373, it has been proposed to use the following as moisture absorbents:
- particles of water-soluble polymers of natural origin, such as carraghenates, starches, guar gum, agar, low pectin esters, furcellaran, gelatin, xanthan gum, hydroxypropylmethylcellulose, sodium carboxymethylcellulose, or mixtures thereof;
- particles of synthetic water-soluble polymers, such as polyvinyl alcohol, polyvinylpyrrolidone, polyethylene oxides, carboxyvinyl polymers, copolymers of methyl vinyl ether and maleic anhydride, linear ionenes, or mixtures thereof;
- particles of water-insoluble polymers of natural origin, such as mixtures of sodium alginate and calcium alginate, crosslinked dextrans, modified celluloses, alginic acid, calcium alginate, pregelatinized starches, modified starches, starch-hydrolyzed polyacrylonitrile graft copolymers, or mixtures thereof;
- particles of synthetic water-insoluble polymers, such as crosslinked polyacrylamides, crosslinked poly(acrylic acid)s, crosslinked polyhydroxy-methacrylates, crosslinked polyvinyl alcohols, crosslinked polyvinylpyrrolidones, sulphonated polystyrenes crosslinked with divinylbenzene, polyvinylpyridine crosslinked with divinylbenzene, crosslinked ionenes, or mixtures thereof.

Such compositions have also been described in application WO 05/102264.

In patents GB 2003730 and U.S. Pat. No. 4,508,705, it has been proposed in particular to use particles of moisture-absorbent polymers (gelatinized crosslinked starches) having a water absorption coefficient of at least 2, combined with surfactants having a melting point of from 30 to 75° C. and an organic solvent which partially solubilizes the polymer; the aim being to replace aluminium salts. U.S. Pat. No. 4,743,440 describes particles of modified cellulose used in place of or in combination with aluminium salts.

In patent GB 2067404, hydrocolloids such as, for example, polysaccharides modified with acrylic derivatives, acrylamide, acrylonitrile, or PVA, or crosslinked acrylic polymers (Permasorb 30) have been recommended as moisture absorbents.

Application WO 05/44213 describes solid antiperspirant compositions based on superabsorbent polymers of the grafted starch type, such as Water lock superabsorbent C200. This type of polymer can be combined with sesquiterpene, with zinc oxide and with a volatile silicone.

In applications EP 1258290, EP 1561455 and EP 1561456, it has been proposed to use silicone-grafted hydrophilic polymers capable of swelling in the presence of water while at the same time having a dry feel due to the coating with silicones.

Application EP 1338268 also describes deodorant compositions combining a dialkyl carbonate with moisture absorbents such as starches, silicates or talc. However, the anti-wetness effectiveness and the cosmetic properties obtained with these compositions are not yet entirely satisfactory. Some moisture-absorbing polymers have a tendency to form dry pellets under the arm after application.

There remains therefore the need to search for new formulations for the treatment of perspiration which do not have the drawbacks encountered with those known to date and which provide improved anti-wetness effectiveness and improved cosmetic properties. There is therefore a need to search for new antiperspirant active agents which can replace aluminium salts and aluminium/zirconium salts, which are effective, which can be readily formulated and which are well tolerated.

The Applicant has discovered, surprisingly, that particles constituted of a particular expanded amorphous mineral material make a good agent for treating perspiration and can be readily formulated in many products for use in reducing perspiration, without it being necessary to use conventional astringent salts.

Surprisingly, the Applicant has discovered that the use of particles constituted of an expanded amorphous mineral material comprising at least two elements chosen from silicon, aluminium and magnesium makes it possible to achieve this objective.

The Applicant has also discovered, in particular, that the use of particles of an expanded amorphous mineral material derived from at least one volcanic rock makes it possible to solve the technical problem mentioned above.

The Applicant has discovered more particularly that the use of particles of expanded perlite makes it possible to achieve this objective.

Antiperspirant products are generally provided in the form of an oil/water or water/oil emulsion, or in the form of aqueous or anhydrous sticks, of gels or of aerosols.

Among the roll-ons or the creams available on the antiperspirant product market, three major types of formulation exist: anhydrous or soft solid formulations, water-in-oil emulsions and oil-in-water emulsions. The soft solid anhydrous formulations and the water-in-oil emulsions, which are carriers comprising a continuous oily phase, have the drawback of producing a greasy feel on application.

The antiperspirant compositions currently on the market have the following drawbacks:

a) a wet effect on application that can lead to product transfer on contact with clothing and which is due to drying being too slow;

b) a tacky effect due to the presence of antiperspirant salts which are in the dissolved state in the aqueous phase. This feeling of tackiness and this drying time which is too long are often linked to a feeling of stickiness approaching the feeling of perspiration;

c) a greasy effect due to the presence of oils.

There also remains the need to search for new formulations for the treatment of perspiration, the drying time of which is substantially more rapid and the tacky effect of which is substantially reduced.

In order to solve this technical problem, it has already been proposed, in patent EP 1584330, to use micronized waxes, in particular of polyethylene, having a particle size of less than 50 µm and a melting point above 80° C.

In application US 20040076699, it has been proposed to use bismuth oxychloride, in an aluminium-salt-based composition, in order to give the carrier a dry feeling and a silky effect on the skin. However, bismuth oxychloride is a white pigment, application of which to the armpits should be avoided.

The Applicant has also discovered, surprisingly, that, by combining particles constituted of an expanded mineral material, as described above, with an antiperspirant salt or complex, antiperspirant formulations making it possible to achieve these objectives are obtained.

A subject of the present invention is therefore a cosmetic method for treating perspiration and, optionally, the body odours related to human perspiration, in particular underarm odours, an effective amount of particles of an expanded amorphous mineral material or a composition containing said particles in a cosmetically acceptable carrier, and more particularly of expanded perlite particles.

A subject of the present invention is also a cosmetic method for treating perspiration and, optionally, the body odours related to human perspiration, especially underarm odours, an effective amount of particles of a composition containing, in a cosmetically acceptable carrier, at least said particles and at least one antiperspirant salt or complex.

A subject of the present invention is also a composition containing, in a cosmetically acceptable carrier, at least said particles and at least one antiperspirant salt or complex.

A subject of the present invention is also an anhydrous solid composition in the form of a stick, characterized in that it comprises, in a cosmetically acceptable carrier:

(i) more than 1% by weight, relative to the total weight of the composition, of expanded mineral particles as defined above; and (ii) at least one fatty phase comprising at least one volatile oil and/or at least one non-volatile oil and a structuring agent.

Other subjects of the invention will appear in the subsequent description.

The term "cosmetically acceptable" is intended to mean compatible with the skin and/or its appendages, which has a pleasant colour, odour and feel and which does not create unacceptable discomfort (tingling, tautness, redness), that may discourage the consumer from using this composition.

The term "agent for treating perspiration" is intended to mean any substance which, by itself, has the effect of reducing the feeling of wetness, linked to human sweat, on the skin, or of masking human sweat.

For the purpose of the invention, the term "mineral material" is intended to mean any material constituted of inorganic substances.

The term "amorphous" is intended to mean any material comprising less than 10% by weight of crystalline phase, and preferably less than 5% by weight of crystalline phase, or which is even completely noncrystalline and does not have an ordered atomic structure.

The term "expanded material" is intended to mean any material having an untamped apparent density at 25° C. ranging from 10 to 400 kg/m$^3$ (DIN Standard 53468). This density may in particular be the result of a treatment by means of a thermal process, in particular at a temperature ranging from 700 to 1500° C., and preferably from 800 to 1100° C.

Expanded Amorphous Mineral Material

The expanded amorphous mineral material in accordance with the invention contains at least two elements chosen from silicon, aluminium and magnesium.

The expanded mineral material derived from at least one volcanic rock in accordance with the present invention generally contains, in its composition, at least two elements chosen from silicon, aluminium and magnesium. It is generally obtained by thermal expansion of a volcanic rock comprising from 1% to 10% by weight of water, and preferably from 1% to 5% by weight of water, and less than 10% by weight of crystalline rock, relative to the total weight of the composition of the rock, preferably followed by milling. The temperature of the expansion process can range from 700 to 1500° C., and preferably from 800 to 1100° C. The expansion process described in U.S. Pat. No. 5,002,698 can in particular be used.

Volcanic or "effusive" rocks are generally produced by rapid cooling of the magmatic liquid on contact with air or water (immersion phenomenon giving hyaline rock). The volcanic rocks that can be used according to the present invention are chosen from those defined according to the Streckeisen classification (1974).

Among these volcanic rocks, mention may in particular be made of trachytes, latites, andesites, basalts, rhyolites and dacites. Use will more particularly be made of rhyolites and dacites, and even more particularly of rhyolites.

According to one particular embodiment of the invention, the particles of expanded amorphous mineral material have an expansion coefficient of from 2 to 70.

Preferably, the particles of expanded amorphous mineral material have an untamped density at 25° C. ranging from 10 to 400 kg/m$^3$ (DIN Standard 53468).

According to one particular embodiment of the invention, the particles of expanded amorphous mineral material have a spontaneous pH measured at 25° C., in a dispersion in water at 10% by weight, ranging from 6 to 8.

According to another particular embodiment of the invention, the particles of expanded amorphous mineral material have a silica content of greater than or equal to 65% by weight relative to the total weight of the composition of the material.

According to another particular embodiment of the invention, the particles of expanded amorphous mineral material have a particle size defined by a median diameter $D_{50}$ ranging from 0.5 to 50 µm, and preferably from 0.5 to 40 µm.

Preferably, the particles of expanded amorphous mineral material have a platelet shape.

According to one particular form of the invention, particles of expanded perlite will be chosen as particles of an expanded amorphous material.

The perlites that can be used according to the invention are generally aluminosilicates of volcanic origin and have the composition:
- 70.0-75.0% by weight of silica $SiO_2$
- 12.0-15.0% by weight of aluminium oxide $Al_2O_3$
- 3.0-5.0% of sodium oxide $Na_2O$
- 3.0-5.0% of potassium oxide $K_2O$
- 0.5-2% of iron oxide $Fe_2O_3$→
- 0.2-0.7% of magnesium oxide MgO
- 0.5-1.5% of calcium oxide CaO
- 0.05-0.15% of titanium oxide $TiO_2$ The perlite is milled, dried, and then graded in a first step. The product obtained, termed Perlite Ore, is grey in colour and of the order of 100 μm in size.

The Perlite Ore is then expanded (1000° C./2 seconds) so as to give particles that are more or less white. When the temperature reaches 850-900° C., the water trapped in the structure of the material vaporizes and causes expansion of the material relative to its initial volume. The expanded perlite particles in accordance with the invention can be obtained by means of the expansion process described in U.S. Pat. No. 5,002,698.

Preferably, the perlite particles used will be milled; in this case, they are termed expanded milled perlite (EMP). They preferably have a particle size defined by a median diameter $D_{50}$ ranging from 0.5 to 50 μm, and preferably from 0.5 to 40 μm.

Preferably, the perlite particles used have an untamped apparent density at 25° C. ranging from 10 to 400 kg/m$^3$ (DIN Standard 53468), and preferably from 10 to 300 kg/m$^3$.

Preferably, the particles of expanded perlite according to the invention have a water absorption capacity, measured at the Wet Point, ranging from 200% to 1500%, and preferably from 250% to 800%.

The Wet Point corresponds to the amount of water that must be added to 1 g of particle in order to obtain a homogeneous paste. This method derives directly from the oil uptake method applied to solvents. The measurements are carried out in the same way by means of the Wet Point and of the Flow Point having, respectively, the following definition:

Wet Point: mass, expressed in grams per 100 g of product, corresponding to the obtaining of a homogeneous paste when a solvent is added to a powder.

Flow Point: mass, expressed in grams per 100 g, of product starting from which the amount of solvent is greater than the capacity of the powder to retain it. This is reflected by a more or less homogeneous mixture that flows on the glass plate being obtained.

The Wet Point and the Flow Point are measured according to the following protocol:

Protocol for Measuring Water Absorption:
1) Material Used
   Glass plate (25×25 mm)
   Spatula (wooden handle and metal part (15×2.7 mm)
   Brush with silk hairs
   Balance
2) Procedure The glass plate is placed on the balance and 1 g of perlite particles is weighed out. The beaker containing the solvent and also the sampling liquipipette (squeezable plastic pipette) are placed on the balance. The solvent is gradually added to the powder, the whole being mixed regularly (every 3 to 4 drops) using the spatula. The mass of solvent required to obtain the Wet Point is noted. The solvent is again added and the mass required to reach the Flow Point is noted. The mean over 3 tests will be established.

The particles of expanded perlite that are sold under the trade names Optimat 1430 OR or Optimat 2550 by the company World Minerals will in particular be used.

The amount of particles of expanded amorphous mineral used according to the invention may advantageously represent from 1% to 100%, and in particular from 5% to 60%, by weight, of the total weight of the composition.

Galenical Forms

The composition according to the invention may be in any of the galenical forms conventionally used for topical application, and in particular in the form of aqueous gels, aqueous solutions or aqueous-alcoholic solutions. Through the addition of a fatty or oily phase, they may also be in the form of dispersions of the lotion type, of emulsions of liquid or semi-liquid consistency of the milk type, obtained by dispersion of a fatty phase in an aqueous phase (O/W), or conversely (W/O), or of suspensions or emulsions of soft, semi-solid or solid consistency of the cream or gel type, or alternatively of multiple emulsions (W/O/W or O/W/O), of microemulsions, of vesicular dispersions of ionic and/or nonionic type, or of wax/aqueous phase dispersions. These compositions are prepared according to the usual methods.

The invention also relates to compositions packaged in pressurized form in an aerosol device or in a pump-dispenser bottle; packaged in a device fitted with a perforated wall, in particular a grille; or packaged in a roll-on device; characterized in that they contain at least particles of perlite as defined above. In this regard, they contain the ingredients generally used in products of this type, which are well known to those skilled in the art.

The compositions according to the invention intended for cosmetic use may comprise at least one aqueous phase. They are in particular formulated as aqueous lotions, or as a water-in-oil or oil-in-water emulsion, or as a multiple emulsion (oil-in-water-in-oil or water-in-oil-in-water triple emulsion (such emulsions are known and described, for example, by C. Fox in "Cosmetics and Toiletries", November 1986, Vol. 101, pages 101-112)).

Aqueous Phase

The aqueous phase of said compositions contains water and, in general, other water-soluble or water-miscible solvents. The water-soluble or water-miscible solvents include short-chain monoalcohols, for example of $C_1$-$C_4$, such as ethanol or isopropanol; diols or polyols, such as ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether and sorbitol. Propylene glycol, glycerol and propane-1,3-diol will more particularly be used.

Emulsifiers a) Oil-in-Water Emulsifiers

As emulsifiers that may be used in the oil-in-water emulsions or oil-in-water-in-oil triple emulsions, mention may, for example, be made of nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof such as the mixture of glyceryl stearate and PEG-40 stearate.

Mention may also be made of the fatty alcohol/alkylpolyglycoside emulsifier mixtures as described in applications WO 92/06778, WO 95/13863 and WO 98/47610, such as the commercial products sold by the company SEPPIC under the name Montanov®.

b) Water-in-Oil Emulsifiers

Among the emulsifiers that can be used in the water-in-oil emulsions or water-in-oil-in-water-in-oil triple emulsions or triple emulsions, mention may, by way of example, be made of the alkyl dimethicone copolyols corresponding to formula (I) below:

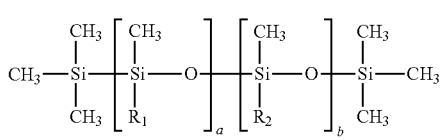

(I)

in which:

$R_1$ denotes a $C_{12}$-$C_{20}$, and preferably $C_{12}$-$C_{18}$, linear or branched alkyl group;

$R_2$ denotes the group: $-C_nH_{2n}-(-OC_2H_4-)_x-(-OC_3H_6-)_y-O-R_3$;

$R_3$ denotes a hydrogen atom or a linear or branched alkyl radical containing from 1 to 12 carbon atoms;

a is an integer ranging from 1 to approximately 500;

b denotes an integer ranging from 1 to approximately 500;

n is an integer ranging from 2 to 12, and preferably 2 to 5;

x denotes an integer ranging from 1 to approximately 50, and preferably from 1 to 30;

y denotes an integer ranging from 0 to approximately 49, and preferably from 0 to 29, with the proviso that, when y is different from zero, the ratio x/y is greater than 1, and preferably ranges from 2 to 11.

Among the preferred alkyl dimethicone copolyol emulsifiers of formula (I), mention will more particularly be made of Cetyl PEG/PPG-10/1 Dimethicone, and more particularly the mixture Cetyl PEG/PPG-10/1 Dimethicone and Dimethicone (INCI name), for instance the product sold under the trade name Abil EM90 by the company Goldschmidt, or else the (Polyglyceryl-4-Stearate and Cetyl PEG/PPG-10 (and) Dimethicone (and) Hexyl Laurate) mixture, for instance the product sold under the trade name Abil WE09 by the same company.

Among the water-in-oil emulsifiers, mention may also be made of the dimethicone copolyols corresponding to formula (II) below:

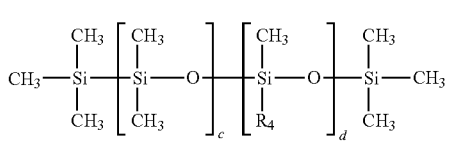

(II)

in which:

$R_4$ denotes the group: $-C_mH_{2m}-(-OC_2H_4-)_s-(-OC_3H_6-)_t-O-R_5$;

$R_5$ denotes a hydrogen atom or a linear or branched alkyl radical containing from 1 to 12 carbon atoms;

c is an integer ranging from 1 to approximately 500;

d denotes an integer ranging from 1 to approximately 500;

m is an integer ranging from 2 to 12, and preferably 2 to 5;

s denotes an integer ranging from 1 to approximately 50, and preferably from 1 to 30;

t denotes an integer ranging from 0 to approximately 50, and preferably from 0 to 30;

with the proviso that the sum s+t is greater than or equal to 1.

Among these preferred dimethicone copolyol emulsifiers of formula (II), use will particularly be made of PEG-18/PPG-18 Dimethicone, and more particularly the Cyclopentasiloxane (and) PEG-18/PPG-18 Dimethicone mixture (INCI name), such as the product sold by the company Dow Corning under the trade name Silicone DC 5225 C, or KF-6040 from the company Shin Etsu.

According to one particularly preferred embodiment, a mixture of at least one emulsifier of formula (I) and at least one emulsifier of formula (II) will be used.

Use will more particularly be made of a mixture of PEG-18/PPG-18 Dimethicone and Cetyl PEG/PPG-10/1 Dimethicone, and even more particularly a mixture of (Cyclopentasiloxane (and) PEG-18/PPG-18 Dimethicone) and of Cetyl PEG/PPG-10/1 Dimethicone and Dimethicone or of (Polyglyceryl-4-stearate and Cetyl PEG/PPG-10 (and) Dimethicone (and) Hexyl Laurate).

Among the water-in-oil emulsifiers, mention may also be made of nonionic emulsifiers derived from a fatty acid and from a polyol, alkylpolyglycosides (APGs), sugar esters, and mixtures thereof.

As nonionic emulsifiers derived from a fatty acid and from a polyol, use may in particular be made of fatty acid esters of a polyol, the fatty acid having in particular a $C_8$-$C_{24}$ alkyl chain, and the polyols being, for example, glycerol and sorbitan.

As fatty acid esters of a polyol, mention may in particular be made of isostearic acid esters of polyols, stearic acid esters of polyols, and mixtures thereof, in particular isostearic acid esters of glycerol and/or of sorbitan.

As stearic acid esters of polyols, mention may in particular be made of polyethylene glycol esters, for instance PEG-30 dipolyhydroxystearate, such as the product sold under the name Arlacel P135 by the company ICI.

As glycerol and/or sorbitan esters, mention may, for example, be made of polyglycerol isostearate, such as the product sold under the name Isolan GI 34 by the company Goldschmidt; sorbitan isostearate, such as the product sold under the name Arlacel 987 by the company ICI; glycerol sorbitan isostearate, such as the product sold under the name Arlacel 986 by the company ICI; the mixture of sorbitan isostearate and polyglycerol isostearate (3 mol) sold under the name Arlacel 1690 by the company Uniqema, and mixtures thereof.

The emulsifier may also be chosen from alkylpolyglycosides having an HLB of less than 7, for example those represented by general formula (1) below:

(1)

in which R represents a branched and/or unsaturated alkyl radical containing from 14 to 24 carbon atoms, G represents a reduced sugar containing from 5 to 6 carbon atoms, and x denotes a value ranging from 1 to 10, and preferably from 1 to 4, and G denotes in particular glucose, fructose or galactose.

The unsaturated alkyl radical may comprise one or more ethylenic unsaturations, and in particular one or two ethylenic unsaturations.

As alkylpolyglycosides of this type, mention may be made of alkylpolyglucosides (G=glucose in formula (1)), and in particular the compounds of formula (1) in which R represents more particularly an oleyl radical (unsaturated $C_{18}$ radical) or an isostearyl radical (saturated $C_{18}$ radical), G denotes glucose, x is a value ranging from 1 to 2, in particular isostearylglucoside, oleylglucoside and mixtures thereof. This alkylpolyglucoside may be used as a mixture with a coemulsifier, more especially with a fatty alcohol, and in particular a fatty alcohol having the same fatty chain as that of the alkylpolyglucoside, i.e. containing from 14 to 24 carbon atoms, and having a branched and/or unsaturated chain, and for example isostearyl alcohol when the alkylpolyglucoside is isostearylglucoside, and oleyl alcohol when the alkylpolyglucoside is oleylglucoside, optionally in the form of a self-emulsifying composition, as described, for example, in document WO-A-92/06778. The mixture of isostearylglucoside and isostearyl alcohol sold under the name Montanov WO 18 by the company SEPPIC, and also the octyldodecanol and octyldodecylxyloside mixture sold under the name Fludanov 20× by the company SEPPIC, may, for example, be used.

Mention may also be made of polyolefins with a succinic end group, such as polyisobutylenes with an esterified succinic end group and salts thereof, in particular the diethanolamine salts, such as the products sold under the names Lubrizol 2724, Lubrizol 2722 and Lubrizol 5603 by the company Lubrizol or the commercial product Chemcinnate 2000.

The total amount of emulsifiers in the composition will preferably, in the composition according to the invention, be at contents with respect to active material ranging from 1% to 8% by weight, and more particularly from 2% to 6% by weight, relative to the total weight of the composition.

According to another particular form of the invention, the compositions according to the invention may be anhydrous.

The term "anhydrous composition" is intended to mean a composition containing less than 2% by weight of water, or even less than 0.5% by weight of water, and in particular free of water, the water not being added during the preparation of the composition, but corresponding to the residual water provided by the ingredients mixed.

According to another particular subject of the invention, the compositions of the invention are anhydrous solid compositions in the form of a stick, characterized in that they comprise, in a cosmetically acceptable carrier:

(i) more than 1% by weight, relative to the total weight of the composition, of expanded mineral particles as defined above; and (ii) at least one fatty phase comprising at least one volatile oil and/or at least one non-volatile oil and a structuring agent.

The term "solid composition" is intended to mean that the measurement of the maximum force measured by texturometry during insertion of a probe down into the formulation sample should be at least equal to 0.25 newton, in particular at least equal to 0.30 newton, especially at least equal to 0.35 newton, assessed under precise measuring conditions as follows.

The formulations are hot-cast into pots 4 cm in diameter and 3 cm deep. Cooling is at ambient temperature. The hardness of the formulations prepared is measured after a standing period of 24 hours. The pots containing the samples are characterized by texturometry using a texturometer such as that sold by the company Rheo TA-XT2, according to the following protocol: a probe of steel bead type, 5 mm in diameter, is brought into contact with the sample at a speed of 1 mm/s. The measuring system detects the interface with the sample with a detection threshold equal to 0.005 newton. The probe is pushed down 0.3 mm into the sample, at a speed of 0.1 mm/s. The measuring apparatus records the change in compression force measured over time, during the penetration phase. The hardness of the sample corresponds to the average of the maximum values of the force detected during the penetration, over at least 3 measurements.

According to one particular form of the invention, the compositions for treating perspiration according to the invention may also be in the form of a loose or compacted powder.

Fatty Phase

The compositions according to the invention may contain at least one water-immiscible organic liquid phase, called fatty phase. The latter comprises, in general, one or more hydrophobic compounds which render said phase water-immiscible. Said phase is liquid (in the absence of structuring agent) at ambient temperature (20-25° C.). Preferably, the water-immiscible organic liquid phase in accordance with the invention generally comprises at least one volatile oil and/or one non-volatile oil and, optionally, at least one structuring agent.

The term "oil" is intended to mean a fatty substance which is liquid at ambient temperature (25° C.) and atmospheric pressure (760 mmHg, i.e. $10^5$ Pa). The oil may be volatile or non-volatile.

For the purpose of the invention, the term "volatile oil" is intended to mean an oil capable of evaporating on contact with the skin or with the keratin fibre in less than one hour, at ambient temperature and atmospheric pressure. The volatile oils of the invention are volatile cosmetic oils which are liquid at ambient temperature and which have a non-zero vapour pressure, at ambient temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg), and more particularly ranging from 1.3 Pa to 1300 Pa (0.01 to 10 mmHg).

The term "non-volatile oil" is intended to mean an oil which remains on the skin or the keratin fibre at ambient temperature and atmospheric pressure for at least several hours and which has in particular a vapour pressure of less than $10^{-3}$ mmHg (0.13 Pa).

The oil may be chosen from any of the physiologically acceptable, and in particular cosmetically acceptable, oils, especially mineral, animal, plant or synthetic oils; in particular, volatile or non-volatile, hydrocarbon-based and/or silicone and/or fluoro oils and mixtures thereof.

More specifically, the term "hydrocarbon-based oil" is intended to mean an oil comprising mainly carbon and hydrogen atoms and, optionally, one or more functions chosen from hydroxyl, ester, ether and carboxylic functions. Generally, the oil has a viscosity of from 0.5 to 100 000 mPa·s, preferably from to 50 000 mPa·s, and more preferably from 100 to 30 000 mPa·s.

By way of example of a volatile oil that can be used in the invention, mention may be made or:

volatile hydrocarbon-based oils chosen from hydrocarbon-based oils containing from 8 to 16 carbon atoms, and in particular $C_8$-$C_{16}$ isoalkanes of petroleum origin (also known as isoparaffins), such as isododecane (also known as 2,2,4,4,6-pentamethylheptane), isodecane or isohexadecane, and for example the oils sold under the trade names Isopars or Permetyls, $C_8$-$C_{16}$ branched esters, isohexyl neopentanoate, and mixtures thereof. Other volatile hydrocarbon-based oils, such as petroleum distillates, in particular those sold under the name Shell Solt by the company Shell, may also be used; volatile linear alkanes such as those described in patent application DE 10 2008 012 457 from the company Cognis;

volatile silicones, for instance volatile linear or cyclic silicone oils, in particular those having a viscosity ≤8 centistokes ($8 \times 10^{-6}$ m$^2$/s), and having in particular from 2 to 7 silicon atoms, these silicones optionally comprising alkyl or alkoxy groups containing from 1 to 10 carbon atoms. As volatile silicone oil that can be used in the invention, mention may in particular be made of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane; and mixtures thereof.

Mention may also be made of the linear volatile alkyltrisiloxane oils of general formula (I):

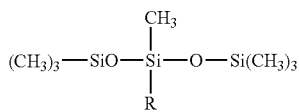

where R represents an alkyl group containing from 2 to 4 carbon atoms, and one or more hydrogen atoms of which may be substituted with a fluorine or chlorine atom.

Among the oils of general formula (I), mention may be made of:
3-butyl-1,1,1,3,5,5,5-heptamethyltrisiloxane,
3-propyl-1,1,1,3,5,5,5-heptamethyltrisiloxane, and
3-ethyl-1,1,1,3,5,5,5-heptamethyltrisiloxane,
corresponding to the oils of formula (I) for which R is, respectively, a butyl group, a propyl group or an ethyl group.

By way of example of a non-volatile oil that can be used in the invention, mention may be made of:

hydrocarbon-based oils of animal origin, such as perhydrosqualene;

plant hydrocarbon-based oils, such as liquid triglycerides of fatty acids containing from 4 to 24 carbon atoms, such as heptanoic or octanoic acid triglycerides, or else wheat germ oil, olive oil, sweet almond oil, palm oil, rapeseed oil, cottonseed oil, alfalfa oil, poppy oil, pumpkin oil, marrow oil, blackcurrant oil, evening primrose oil, millet oil, barley oil, quinoa oil, rye oil, saffron oil, candlenut oil, passion flower oil, musk rose oil, sunflower oil, maize oil, soybean oil, grapeseed oil, sesame oil, hazelnut oil, apricot oil, macadamia oil, caster oil, avocado oil, caprylic/capric acid triglycerides such as those sold by the company Stearineries Dubois or those sold under the names Miglyol 810, 812 and 818 by the company Dynamit Nobel, jojoba oil or shea butter;

linear or branched hydrocarbons of inorganic or synthetic origin, such as liquid paraffins and derivatives thereof, petroleum jelly, polydecenes, polybutenes, hydrogenated polyisobutene such as parleam, or squalane;

synthetic ethers containing from 10 to 40 carbon atoms;

synthetic esters, in particular of fatty acids, such as oils of formula $R_1COOR_2$ in which $R_1$ represents a linear or branched higher fatty acid residue containing from 1 to 40 carbon atoms and $R_2$ represents an in particular branched hydrocarbon-based chain containing from 1 to 4 carbon atoms, with $R_1+R_2 \geq 10$, for instance purcellin oil (cetostearyl octanoate), isononyl isononanoate, isopropyl myristate, isopropyl palmitate, $C_{12}$-$C_{15}$ alkyl benzoate, hexyl laurate, diisopropyl adipate, 2-ethylhexyl palmitate, 2-octyldodecyl stearate, 2-octyldodecyl erucate, isostearyl isostearate, tridecyl trimellitate; alkyl or polyalkyl octanoates, decanoates or ricinoleates such as propylene glycol dioctanoate; hydroxylated esters such as isostearyl lactate, octyl hydroxystearate, octyldodecyl hydroxystearate, diisostearyl malate, triisocetyl citrate, fatty alcohol heptanoates, octanoates and decanoates; polyol esters such as propylene glycol dioctanoate, neopentyl glycol diheptanoate or diethylene glycol diisononanoate; and pentaerythritol esters such as pentaerythrityl tetraisostearate;

fatty alcohols that are liquid at ambient temperature, comprising a branched and/or unsaturated carbon-based chain containing from 12 to 26 carbon atoms, such as octyldodecanol, isostearyl alcohol, 2-butyloctanol, 2-hexyldecanol, 2-undecylpentadecanol or oleyl alcohol;

higher fatty acids such as oleic acid, linoleic acid or linolenic acid;

carbonates;

acetates;

citrates;

fluoro oils, optionally partially hydrocarbon-based and/or silicon-based, such as fluorosilicon oils, fluorinated polyethers or fluorinated silicones, as described in document EP-A-847752;

silicon oils, such as polydimethylsiloxanes (PDMS) which are non-volatile and linear or cyclic; polydimethylsiloxanes comprising alkyl, alkoxy or phenyl groups which are pendant or at the end of the silicone chain, said groups having from 2 to 24 carbon atoms; phenylated silicones such as phenyl trimethicones, phenyl dimethicones, phenyltrimethylsiloxydiphenylsiloxanes, diphenyl dimethicones, diphenylmethyldiphenyltrisiloxanes or 2-(phenylethyl) trimethylsiloxysilicates, and mixtures thereof.

Structuring Agent

The compositions according to the invention comprising a fatty phase may also contain at least one structuring agent for said fatty phase which may be chosen preferably from waxes, pasty compounds, inorganic or organic lipophilic gelling agents, and mixtures thereof.

It is understood that the amount of these compounds may be adjusted by those skilled in the art in such a way as to not be detrimental to the desired effect in the context of the present invention.

Wax(es)

Wax is, in general, a lipophilic compound which is solid at ambient temperature (25° C.), which has a reversible solid/liquid change in state and which has a melting point of greater than or equal to 30° C., which can go up to 200° C. and in particular up to 120° C.

In particular, the waxes suitable for the invention may have a melting point of greater than or equal to 45° C., and in particular greater than or equal to 55° C.

For the purpose of the invention, the melting point corresponds to the temperature of the most endothermic peak observed by thermal analysis (DSC) as described in ISO Standard 11357-3; 1999. The melting point of the wax can be measured using a differential scanning calorimeter (DSC), for example the calorimeter sold under the name "MDSC 2920" by the company TA Instruments.

The measurement protocol is as follows:

A 5 mg sample of wax placed in a crucible is subjected to a first rise in temperature ranging from −20° C. to 100° C. at a heating rate of 10° C./minute, and is then cooled from 100° C. to −20° C. at a cooling rate of 10° C./minute and, finally, is subjected to a second rise in temperature ranging from −20° C. to 100° C. at a heating rate of 5° C./minute. During the second rise in temperature, the variation in the difference in power absorbed by the empty crucible and by the crucible containing the sample of wax is measured as a function of the temperature. The melting point of the compound is the value of the temperature corresponding to the tip of the peak of the curve representing the variation in the difference in power absorbed as a function of the temperature.

The waxes that can be used in the compositions according to the invention are chosen from waxes, which are solid at ambient temperature, of animal, plant, mineral or synthetic origin, and mixtures thereof.

By way of illustration of the waxes suitable for the invention, mention may in particular be made of hydrocarbon-based waxes such as beeswax, lanolin wax, and Chinese insect waxes, rice bran wax, carnauba wax, candelilla wax, ouricury wax, Alfa wax, berry wax, shellac wax, Japan wax and sumach wax; montane wax, orange and lemon waxes, the refined sunflower wax sold under the name Sunflower Wax by Koster Keunen, microcrystalline waxes, paraffins and ozokerites; polyethylene waxes, waxes obtained by Fischer Tropsch synthesis and waxy copolymers, and also esters thereof.

Mention may also be made of waxes obtained by catalytic hydrogenation of animal or plant oils containing linear or branched $C_8$-$C_{32}$ fatty chains. Among these, mention may in particular be made of isomerized jojoba oil such as the trans-isomerized partially hydrogenated jojoba oil manufactured or sold by the company Desert Whale under the commercial reference Iso-Jojoba-50®, hydrogenated sunflower oil, hydrogenated castor oil, hydrogenated coconut oil, hydrogenated lanolin oil, and the di-(1,1,1-trimethylolpropane)tetrastearate sold under the name Hest 2T-4S® by the company Heterene.

Mention may also be made of silicone waxes ($C_{30-45}$ Alkyl Dimethicone) and fluoro waxes.

Use may also be made of the waxes obtained by hydrogenation of castor oil esterified with cetyl alcohol, sold under the names Phytowax ricin 16L64® and 22L73® by the company Sophim. Such waxes are described in application FR-A-2792190.

Use may be made, as wax, of a $C_{20}$-$C_{40}$ alkyl(hydroxystearyloxy)stearate (the alkyl group containing from 20 to 40 carbon atoms), alone or as a mixture.

Such a wax is in particular sold under the names Kester Wax K 82 P®, Hydroxypolyester K 82 P® and Kester Wax K 80 P® by the company Koster Keunen.

As microwaxes that can be used in the compositions according to the invention, mention may in particular be made of carnauba microwaxes such as the product sold under the name MicroCare 350® by the company Micro Powders, microwaxes of synthetic wax, such as the product sold under the name MicroEase 114S® by the company Micro Powders, microwaxes constituted of a mixture of carnauba wax and polyethylene wax, such as those sold under the names MicroCare 300® and 310® by the company Micro Powders, microwaxes constituted of a mixture of carnauba wax and of synthetic wax, such as the product sold under the name MicroCare 325® by the company Micro Powders, polyethylene microwaxes such as those sold under the names Micropoly 200®, 220®, 220L® and 250S® by the company Micro Powders, the commercial products Performalene 400 Polyethylene and Performalene 500-L Polyethylene from New Phase Technologies, Performalene 655 Polyethylene or paraffin waxes such as the wax having the INCI name Microcristalline Wax and Synthetic Wax and sold under the trade name Microlease by the company Sochibo; polytetrafluoroethylene microwaxes such as those sold under the names Microslip 519® and 519 L® by the company Micro Powders.

The composition according to the invention will preferably comprise a content of wax(es) ranging from 3% to 20% by weight, relative to the total weight of the composition, in particular from 5% to 15%, more particularly from 6% to 15%.

According to one particular embodiment of the invention, in the context of the anhydrous solid compositions in the form of a stick, use will be made of polyethylene microwaxes in the form of crystallites having a shape factor at least equal to 2 and having a melting point ranging from 70 to 110° C., and preferably 70 to 100° C., in order to reduce or even eliminate the presence of strata in the solid composition.

These needle-shaped crystallites, and in particular the dimensions thereof, can be characterized visually according to the following method.

The wax is deposited on a microscope slide, which is placed on a heated platform. The slide and the wax are heated to a temperature which is generally at least 5° C. above that of the melting point of the wax or of the wax mixture under consideration. At the end of the melting, the liquid thus obtained and the microscope slide are left to cool in order to solidify. The crystallites are observed using a Leica DMLB100 optical microscope, with an objective selected according to the size of the objects to be visualized, and by polarized light. The dimensions of the crystallites are measured using image analysis software, such as the software sold by the company Microvision.

The crystallite polyethylene waxes in accordance with the invention preferably have an average length ranging from 5 to 10 µm. The term "average length" denotes the dimension given by the statistical particle size distribution to half the population, referred to as D50.

Use will more particularly be made of a mixture of Performalene 400 Polyethylene and Performalene 500-L Polyethylene waxes from New Phase Technologies.

Pasty Compounds

For the purpose of the present invention, the term "pasty compound" is intended to mean a lipophilic fatty compound that undergoes a reversible solid/liquid change of state, that has an anisotropic crystalline organization in the solid state, and that comprises, at a temperature of 23° C., a liquid fraction and a solid fraction.

The pasty compound is preferably chosen from synthetic compounds and compounds of plant origin. A pasty compound may be obtained by synthesis from starting products of plant origin.

The pasty compound may advantageously be chosen from:
  lanolin and derivatives thereof,
  silicone compounds, which may or may not be polymers,
  fluoro compounds, which may or may not be polymers,
  vinylpolymers, in particular:
  olefin homopolymers,
  olefin copolymers,
  hydrogenated diene homopolymers and copolymers, linear or branched oligomers, which are homopolymers or copolymers of alkyl(meth)acrylates preferably containing a $C_8$-$C_{30}$ alkyl group, oligomers, which are homopolymers and copolymers of vinyl esters containing $C_8$-$C_{30}$ alkyl groups, and oligomers, which are homopolymers and copolymers of vinyl ethers containing $C_8$-$C_{30}$ alkyl groups, liposoluble polyethers resulting from the polyetherification between one or more $C_2$-$C_{100}$, preferably $C_2$-$C_{50}$, diols, esters, and mixtures thereof.

Among the esters that are in particular preferred are:

esters of a glycerol oligomer, especially diglycerol esters, in particular condensates of adipic acid and of glycerol, for which some of the hydroxyl groups of the glycerols have reacted with a mixture of fatty acids such as stearic acid, capric acid, stearic acid and isostearic acid, and 12-hydroxystearic acid, in particular such as those sold under the trade mark Softisan 649 by the company Sasol, arachidyl propionate sold under the trade mark Waxenol 801 by Alzo, phytosterol esters, fatty acid triglycerides and derivatives thereof, pentaerythritol esters, noncrosslinked polyesters resulting from polycondensation between a linear or branched $C_4$-$C_{50}$ dicarboxylic acid or polycarboxylic acid and a $C_2$-$C_{50}$ diol or polyol, aliphatic esters of an ester resulting from the esterification of an aliphatic hydroxycarboxylic acid ester with an aliphatic carboxylic acid, polyesters resulting from the esterification, with a polycarboxylic acid, of an aliphatic hydroxycarboxylic acid ester, said ester comprising at least two hydroxyl groups, such as the products Risocast DA-H® and Risocast DA-L®, esters of a diol dimer and of a diacid dimer, where appropriate esterified on their free alcohol or acid function(s) with acid or alcohol radicals, such as Plandool-G, and mixtures thereof.

Among the pasty compounds of plant origin, a mixture of soybean sterols and of oxyethylenated (5 EO) oxypropylenated (5 PO) pentaerythritol, sold under the reference Lanolide by the company Vevy, will preferably be chosen.

Lipophilic Gelling Agents

Mineral Gelling Agents

As mineral lipophilic gelling agent, mention may be made of optionally modified clays such as hectorites modified with a $C_{10}$ to $C_{22}$ ammonium chloride, for instance hectorite modified with distearyldimethylammonium chloride, such as, for example, the product sold under the name Bentone 38V® by the company Elementis.

Mention may also be made of fumed silica, optionally hydrophobically surface-treated, the particle size of which is less than 1 μm. It is in fact possible to chemically modify the surface of the silica, by chemical reaction generating a decrease in the number of silanol groups present at the surface of the silica. It is in particular possible to replace the silanol groups with hydrophobic groups: a hydrophobic silica is then obtained. The hydrophobic groups may be trimethylsiloxyl groups, which are in particular obtained by treatment of fumed silica in the presence of hexamethyldisilazane. Silicas treated in this way are called "Silica Silylate" according to the CTFA (8th Edition, 2000). They are, for example, sold under the references Aerosil R812® by the company Degussa, Cab-O-Sil TS-530® by the company Cabot; dimethylsilyloxyl groups or polydimethylsiloxane groups, which are in particular obtained by treatment of fumed silica in the presence of polydimethylsiloxane or of dimethyldichlorosilane. Silicas treated in this way are called "Silica dimethyl silylate" according to the CTFA (8th Edition, 2000). They are, for example, sold under the references Aerosil R972® and Aerosil R974® by the company Degussa, and Cab-O-Sil TS-610° and Cab-O-Sil TS-720® by the company Cabot.

The hydrophobic fumed silica has in particular a particle size that may be nanometric to micrometric, for example ranging approximately from 5 to 200 nm.

Organic Gelling Agents

The polymeric organic lipophilic gelling agents are, for example, partially or totally crosslinked elastomeric organopolysiloxanes having a three-dimensional structure, such as those sold under the names KSG6®, KSG16® and KSG18® by the company Shin-Etsu, Trefil E-505C® and Trefil E-506C® by the company Dow Corning, Gransil SR-CYC®, SR DMF 10®, SR-DC556®, SR 5CYC gel®, SR DMF 10 gel® and SR DC 556 gel® by the company Grant Industries, and SF 1204® and JK 113® by the company General Electric; ethylcellulose, such as the product sold under the name Ethocel® by the company Dow Chemical; galactomannans comprising from one to six, and in particular from two to four, hydroxyl groups per monosaccharide, substituted with a saturated or unsaturated alkyl chain, such as guar gum alkylated with $C_1$ to $C_6$, and in particular $C_1$ to $C_3$, alkyl chains and mixtures thereof; block copolymers of "diblock", "triblock" or "radial" type, of the polystyrene/polyisoprene or polystyrene/polybutadiene type, such as those sold under the name Luvitol HSB® by the company BASF, of the polystyrene/copoly(ethylenepropylene) type, such as those sold under the name Kraton® by the company Shell Chemical Co, or else of the polystyrene/copoly(ethylene-butylene) type, and blends of triblock and radial (star) copolymers in isododecane, such as those sold by the company Penreco under the name Versagel®, for instance the blend of butylene/ethylene/styrene triblock copolymer and of ethylene/propylene/styrene star copolymer in isododecane (Versagel M 5960).

As lipophilic gelling agent, mention may also be made of polymers with a weight-average molecular weight of less than 100 000, comprising a) a polymeric backbone having hydrocarbon-based repeating units comprising at least one heteroatom and, optionally, b) at least one pendant fatty chain and/or at least one terminal fatty chain, which is optionally functionalized, containing from 6 to 120 carbon atoms and being linked to these hydrocarbon-based units, as described in applications WO-A-02/056847 and WO-A-02/47619, the content of which is incorporated by way of reference; in particular, polyamide resins (especially comprising alkyl groups having from 12 to 22 carbon atoms), such as those described in U.S. Pat. No. 5,783,657, the content of which is incorporated by way of reference.

Among the lipophilic gelling agents that can be used in the compositions according to the invention, mention may also be made of esters of dextrin and of a fatty acid, such as dextrin palmitates, in particular such as those sold under the names Rheopearl TL® or Rheopearl KL® by the company Chiba Flour.

Use may also be made of silicone polyamides of the polyorganosiloxane type, such as those described in documents U.S. Pat. Nos. 5,874,069, 5,919,441, 6,051,216 and 5,981,680.

These silicone polymers may belong to the following two families:
- polyorganosiloxanes comprising at least two groups capable of establishing hydrogen interactions, these two groups being located in the polymer chain, and/or
- polyorganosiloxanes comprising at least two groups capable of establishing hydrogen interactions, these two groups being located on grafts or branches.

Antiperspirant Salts or Complexes

According to one particular embodiment of the invention, the compositions of the invention may contain at least one additional antiperspirant salt or complex.

The antiperspirant salts or complexes in accordance with the invention are generally chosen from aluminium and/or zirconium salts or complexes. They are preferably chosen from aluminium halohydrates; aluminium zirconium halohydrates, complexes of zirconium hydroxychloride and of aluminium hydroxychloride with or without an amino acid, such as those described in U.S. Pat. No. 3,792,068.

Among the aluminium salts, mention may in particular be made of aluminium chlorohydrate in the activated or non-activated form, aluminium chlorohydrex, the aluminium chlorohydrex polyethylene glycol complex, the aluminium chlorohydrex propylene glycol complex, aluminium dichlorohydrate, the aluminium dichlorohydrex polyethylene glycol complex, the aluminium dichlorohydrex propylene glycol complex, aluminium sesquichlorohydrate, the aluminium sesquichlorohydrex polyethylene glycol complex, the aluminium sesquichlorohydrex propylene glycol complex, or aluminium sulphate buffered with sodium aluminium lactate.

Among the aluminium zirconium salts, mention may in particular be made of aluminium zirconium octachlorohydrate, aluminium zirconium pentachlorohydrate, aluminium zirconium tetrachlorohydrate or aluminium zirconium trichlorohydrate.

The complexes of zirconium hydroxychloride and of aluminium hydroxychloride with an amino acid are generally known under the name ZAG (when the amino acid is glycine). Among these products, mention may be made of the aluminium zirconium octachlorohydrex glycine, aluminium zirconium pentachlorohydrex glycine, aluminium zirconium tetrachlorohydrex glycine and aluminium zirconium trichlorohydrex glycine complexes.

The antiperspirant salts or complexes may be present in the composition according to the invention in a proportion of approximately 0.5% to 25% by weight relative to the total weight of the composition.

Deodorant Active Agents

The compositions according to the invention may also contain, in addition, one or more deodorant active agents.

The deodorant active agents may be bacteriostatic agents or bactericidal agents which act on the microorganisms of underarm odours, such as 2,4,4'-trichloro-2'-hydroxydiphenyl ether (Triclosan®), 2,4-dichloro-2'-hydroxydiphenyl ether, 3',4',5'-trichlorosalicylanilide, 1-(3',4'-dichlorophenyl)-3-(4'-chlorophenyl)urea (Triclocarban®) or 3,7,11-trimethyldodeca-2,5,10-trienol (Farnesol®); quaternary ammonium salts such as cetyltrimethylammonium salts or cetylpyridinium salts, DPTA (1,3-diaminopropanetetraacetic acid), 1,2-decanediol (Symclariol from the company Symrise), —glycerol derivatives such as, for example, caprylic/capric glycerides (Capmul MCM from Abitec), glycerol caprylate or caprate (Dermosoft GMCY and Dermosoft GMC respectively from Straetmans), polyglyceryl-2 caprate (Dermosoft DGMC from Straetmans), biguanide derivatives, such as polyhexamethylene biguanide salts, —chlorhexidine and its salts; 4-phenyl-4,4-dimethyl-2-butanol (Symdeo MPP from Symrise).

Among the deodorant active agents in accordance with the invention, mention may also be made of:
- zinc salts, such as zinc salicylate, zinc gluconate, zinc pidolate; zinc sulphate, zinc chloride, zinc lactate, zinc phenolsulphonate; zinc ricinoleate;
- sodium bicarbonate;
- salicylic acid and its derivatives such as 5-n-octanoylsalicylic acid;
- silver zeolites or zeolites without silver;
- alum.

In the event of incompatibility between the active agents mentioned above, or in order to stabilize them, some of said active agents may be incorporated into spherules, in particular ionic or nonionic vesicles and/or nanoparticles (nanocapsules and/or nanospheres).

The deodorant active agents may be present preferably in the compositions according to the invention in weight concentrations ranging from 0.01% to 5% by weight relative to the total weight of the composition.

Suspending Agents

In order to improve the homogeneity of the product, it is possible to use, in addition, one or more suspending agents which are preferably chosen from hydrophobic modified montmorillonite clays, such as hydrophobic modified bentonites or hectorites. Mention may, for example, be made of the product Stearalkonium Bentonite (CTFA name) (reaction product of bentonite and of the quaternary ammonium stearalkonium chloride), such as the commercial product sold under the name Tixogel MP 250 by the company Sud Chemie Rheologicals, United Catalysts Inc., or the product Disteardimonium Hectorite (CTFA name) (reaction product of hectorite and of distearyldimonium chloride), sold under the name Bentone 38 or Bentone Gel by the company Elementis Specialities.

The suspending agents are preferably present in amounts ranging from 0.1% to 5% by weight, and more preferably from 0.2% to 2% by weight, relative to the total weight of the composition.

Organic Powder

According to one particular embodiment of the invention, the antiperspirant compositions according to the invention will also contain an organic powder.

In the present application, the term "organic powder" is intended to mean any solid which is insoluble in the medium at ambient temperature (25° C.)

As organic powders that can be used in the composition of the invention, mention may, for example, be made of polyamide particles, and in particular those sold under the name Orgasol by the company Atochem; polyethylene powders; microspheres based on acrylic copolymers, such as those made of ethylene glycol dimethacrylate/lauryl methacrylate copolymer, sold by the company Dow Corning under the name Polytrap; microspheres of poly(methyl methacrylate), sold under the name Microsphere M-100 by the company Matsumoto or under the name Covabead LH85 by the company Wackherr; hollow poly(methyl methacrylate) microspheres (particle size: 6.5-10.5µ) sold under the name Ganzpearl GMP 0800 by Ganz Chemical; methyl methacrylate/ethylene glycol dimethacrylate copolymer microbeads (size: 6.5-10.5µ) sold under the name Ganzpearl GMP 0820 by Ganz Chemical or Microsponge 5640 by the company Amcol Health & Beauty Solutions; ethylene-acrylate copolymer powders, such as those sold under the name Flobeads by the company Sumitomo Seika Chemicals; expanded powders such as hollow microspheres, and in particular the microspheres formed from a vinylidene chloride/acrylonitrile/methacrylate terpolymer and sold under the name Expancel by the company Kemanord Plast under the references 551 DE 12 (particle size of approximately 12 µm and density 40 kg/m$^3$), 551 DE 20 (particle size of approximately 30 µm and density 65 kg/m$^3$), and 551 DE 50 (particle size of approximately 40 µm), or the microspheres sold under the name Micropearl F 80 ED by the company Matsumoto; powders of natural organic materials, such as starch powders, in particular crosslinked or noncrosslinked maize, wheat or rice starch powders, such as the powders of starch crosslinked with octenylsuccinic anhydride, sold under the name Dry-Flo by the company National Starch; silicone resin microbeads such as those sold under the name Tospearl by the company Toshiba Silicone, in particular Tospearl 240; amino acid powders such as the lauroyllysine powder sold under the name Amihope LL-11 by the company Ajinomoto; particles of wax microdispersion, which preferably have average sizes of less than 1 µm, and in particular ranging from 0.02 µm to 1 µm, and which are essentially constituted of a wax or of a mixture of waxes, such as the products sold under the name Aquacer by the company Byk Cera, and in particular: Aquacer 520 (mixture of synthetic and natural waxes), Aquacer 514 or 513 (polyethylene wax), Aquacer 511 (polymeric wax), or such as the products sold under the name Jonwax 120 by the company Johnson Polymer (mixture of polyethylene and paraffin waxes) and under the name Ceraflour 961 by the company Byk Cera (micronized modified polyethylene wax); and mixtures thereof.

Additives

The cosmetic compositions according to the invention may also comprise cosmetic adjuvants chosen from emollients, antioxidants, opacifiers, stabilizers, moisturizers, vitamins, bactericides, preservatives, polymers, fragrances, thickeners, propellants or any other ingredient normally used in cosmetics for this type of application.

Of course, those skilled in the art will take care to select this or these optional additional compound(s) in such a way that the advantageous properties intrinsically associated with the cosmetic composition in accordance with the invention are not, or are not substantially, impaired by the addition(s) envisaged.

The thickeners, preferably nonionic thickeners, may be chosen from modified or nonmodified guar gums and celluloses, such as hydroxypropyl guar gum or cetylhydroxyethylcellulose, and silicas, for instance Bentone Gel MIO sold by the company NL Industries or Veegum Ultra sold by the company Polyplastic.

The thickeners may also be cationic, such as, for example, the Polyquaternium-37 sold under the name Salcare SC95 (polyquaternium-37 (and) mineral oil (and) PPG-1 trideceth-6) or Salcare SC96 (polyquaternium-37 (and) propylene glycol dicaprylate/dicaprate (and) PPG-1-trideceth-6), or other crosslinked cationic polymers such as, for example, those having the CTFA name ethyl acrylate/dimethylamino ethyl methacrylate cationic copolymer in emulsion.

The amounts of these various constituents that may be present in the cosmetic composition according to the invention are those conventionally used in compositions for the treatment of perspiration.

Aerosols

The compositions according to the invention may also be pressurized and be packaged in an aerosol device constituted of:

(A) a container comprising an antiperspirant composition as defined above, (B) at least one propellant and a means of dispensing said aerosol composition.

The propellants generally used in products of this type, and which are well known to those skilled in the art, are, for instance, dimethyl ether (DME), volatile hydrocarbons such as n-butane, propane or isobutane, and mixtures thereof, optionally with at least one chlorinated and/or fluorinated hydrocarbon; among the latter, mention may be made of the compounds sold by the company Dupont de Nemours under the names Fréon® and Dymel®, and in particular monofluorotrichloromethane, difluorodichloromethane, tetrafluorodichloroethane and 1,1-difluoroethane, sold in particular under the trade name Dymel 152 A by the company Dupont. Carbon dioxide, nitrous oxide, nitrogen or compressed air may also be used as propellant.

The compositions containing the perlite particles as defined above and the propellant(s) may be in the same compartment or in different compartments in the aerosol container. According to the invention, the pressurized concentration of propellant generally ranges from 5% to 95% by weight, and more preferably from 50% to 85% by weight, relative to the total weight of the pressurized composition.

The dispensing means, which forms part of the aerosol device, is generally constituted of a dispensing valve controlled by a dispensing head, itself comprising a nozzle via which the aerosol composition is vaporized. The container containing the pressurized composition may be opaque or transparent. It may be made of glass, of polymer or of metal, optionally covered with a layer of protective lacquer.

The examples which follow serve to illustrate the present invention. The amounts are given as percentage by mass relative to the total weight of the composition.

EXAMPLES 1 TO 6

Roll-Ons

Comparative Stickiness and Drying Test

Protocol

A texture analyser having the following characteristics is used:

Instrument: Texture Expert TA-XT2 by Rheo

Presettings:

Rotor: 10 mm ebonite cylinder

Descent prerate of the rotor 2 mm/s

Descent rate of the rotor 10 mm/s

Ascent rate of the rotor 5 mm/s

Force exerted on the glass plate: 40 g

Displacement: 0.5 mm

Time 1.5 s

Activating force 20 g

Acquisition rate 200 pps

Each antiperspirant is applied, with a film drawer, to a glass plate. The maximum adhesive force exerted by the rotor, which corresponds to the strength of the stickiness, is measured every minute and the rotor is cleaned after each measurement.

This operation is carried out until the maximum force is zero, i.e. until completion of the drying. The drying time is determined at this precise moment.

The results of the tests are represented in Figure 1 by the curve of variation in the strength of the stickiness as a function of time, and in the following Tables 1 and 2:

TABLE 1

| Ingredients (INCI name) | Example 1 Roll-on (not part of the invention) | Example 2 Roll-on (not part of the invention) | Example 3 Roll-on (invention) |
|---|---|---|---|
| Aluminium Chlorohydrate Chlorhydrol 50 (Summit Reheis) | 30 | 30 | 30 |
| Expanded Milled Perlite (Optimat 1430 OR - World Minerals) | 0 | 0 | 1 |
| Silica Aerosil 200 (Evonik Degussa) | 0 | 1 | 0 |
| Polydimethylsiloxane (Viscosity: 350 CST) (Dow Corning 200 Fluid 350 CST - Dow Corning) | 0.5 | 0.5 | 0.5 |
| Cetearyl Alcohol | 2.5 | 2.5 | 2.5 |
| Ceteareth-33 | 1.25 | 1.25 | 1.25 |
| PPG-15 Stearyl Ether (Arlamol E Croda) | 3 | 3 | 3 |
| Deionized water | qs 100 | qs 100 | qs 100 |
| FORCE (g) max at 1 minute | 37 | 28 | 20 |
| Drying speed (min) | 8 | 7 | 6 |

It was found that the addition of 1% of perlite to a roll-on emulsion greatly decreases the stickiness and accelerates the drying speed.

TABLE 2

| Ingredients (INCI name) | Example 4 Roll-on (not part of the invention) | Example 5 Roll-on (not part of the invention) | Example 6 Roll-on (invention) |
|---|---|---|---|
| Aluminium Chlorohydrate Chlorhydrol 50 (Summit Reheis) | 30 | 30 | 30 |
| Expanded Milled Perlite (Optimat 1430 OR - World Minerals) | 0 | 0 | 1 |
| Silica Aerosil 200 (Evonik Degussa) | 0 | 1 | 0 |
| Steareth-100/PEG-136/HDI copolymer (Rheolate FX 1100 - Elementis) | 1 | 1 | 1 |
| Polydimethylsiloxane (Viscosity: 350 CST) (Dow Corning 200 Fluid 350 CST - Dow Corning) | 0.5 | 0.5 | 0.5 |
| C14-22 Alcohols (And) C12-20 alkyl glucoside Montanov L (Seppic) | 2.5 | 2.5 | 2.5 |
| Preservative | qs | qs | qs |
| Deionized water | qs 100 | qs 100 | qs 100 |
| FORCE (g) max at 1 minute | 40 | 32 | 22 |
| Drying speed (min) | 5 | 4 | 3 |

It was found that the addition of 1% perlite to a roll-on emulsion greatly decreases the stickiness (50%) and accelerates the drying speed (25% more rapid).

EXAMPLES 7 TO 9

Anhydrous Aerosols

Comparative Stickiness and Drying Test

The Same Protocol as that Implemented with Examples 11 to 16 is Used

The results of the tests are represented in Figure 2 by the curve of variation in strength of the stickiness as a function of time and in Table 3 below:

TABLE 3

| Ingredients (INCI name) | Example 7 Aerosol (not part of the invention) | Example 8 Aerosol (not part of the invention) | Example 9 Aerosol (invention) |
|---|---|---|---|
| Aluminium chlorohydrate (Reach 103 - Summit Reheis) | 5.25 | 5.25 | 5.25 |
| Stearalkonium Bentonite (Tixogel MP 250 - Rockwood Additives) | 0.39 | 0.39 | 0.39 |
| Expanded Milled Perlite (Optimat 1430 OR - World Minerals) | 0 | 0 | 1 |
| Silica Aerosil 200 (Evonik Degussa) | 0 | 0.20 | 0 |
| Isopropyl Palmitate | 0.90 | 0.90 | 0.90 |
| Cyclopentasiloxane (and) Dimethiconol (Dow Corning 1501 Fluid - Dow Corning) | 1.35 | 1.35 | 1.35 |
| Triethyl Citrate (Citroflex 2 - Vertellus) | 1.05 | 1.05 | 1.05 |
| Polydimethylsiloxane (Viscosity: 350 CST) (Dow Corning 200 Fluid 350 CST - Dow Corning) | qs | qs | qs |
| Isobutane | 85 | 85 | 85 |
| FORCE (g) max at 1 minute | 27 | 22 | 16 |
| Drying speed (min) | 15 | 14 | 12 |

It was found that the addition of 1% of perlite to a roll-on emulsion greatly decreases the stickiness (50%) and accelerates the drying speed (25% more rapid).

| Ingredients (INCI name) | Example 10 Stick (invention) | Example 11 Stick (invention) |
|---|---|---|
| Polyethylene wax (Performalene 500-L Polyethylene - New Phase Technologies) | 0 | 4.1 |
| Ethylene Homopolymer (Performalene 400 Polyethylene - New Phase Technologies) | 0 | 8.3 |
| Oxypropylenated butyl alcohol (fluid AP, low odor - Amerchol Dow Chemical) | 6.2 | 0 |
| Isopropyl Palmitate | 26.7 | 0 |
| Stearyl alcohol (Lanette 18 - Cognis) | 15 | 0 |

-continued

| Ingredients (INCI name) | Example 10 Stick (invention) | Example 11 Stick (invention) |
|---|---|---|
| Hydrogenated castor oil Cutina HR Pulver (Cognis) | 4 | 0 |
| Polyethylene Glycol Distearate (8 EO) (Dub DS PEG 8 - Stéarineries Dubois) | 6.5 | 0 |
| Phenyl Trimethicone (Dow Corning 556 Cosmetic Grade Fluid - Dow Corning) | 0 | 19.6 |
| Isohexadecane | 0 | 19.6 |
| Cyclopentadimethylsiloxane (Dow Corning 245 Fluid - Dow Corning) | 0 | 0 |
| Cyclohexadimethylsiloxane (Dow Corning 246 Fluid - Dow Corning) | 20.1 | 26.4 |
| Methyl Methacrylate Crosspolymer (Ganzpearl GMP 0820 - Ganz Chemical) | 15 | 15 |
| Expanded Milled Perlite (Optimat 1430 OR - World Minerals) | 6.5 | 6.5 |
| Micronized Zinc Pyrrolidone Carboxylate (UCIB - Solabia) | 0 | 0.5 |
| Appearance control T 24H | Some white strata | Homogeneous stick |

Procedure:

The cyclopentasiloxane is heated to 65° C. The other ingredients are added (one by one) with the temperature remaining at 65-70° C. The whole (transparent solution) is homogenized for 15 minutes. The perlite is added. The mixture is cooled to approximately 55° C. (a few ° C. above thickening of the mixture) and is cast in sticks. The resulting sticks are placed at 4° C. for 30 minutes. The stick of Example 10 exhibits some white strata. It is observed that the combination of the two polyethylene waxes Performalene 500-L polyethylene and Performalene 400 polyethylene from New Phase Technologies makes it possible to obtain a stratum-free stick containing perlite (Example 11).

Comparative Test of Antiperspirant Effectiveness Between a Perlite Stick and a Stick Containing a Superabsorbent

| Ingredients (INCI name) | Example 12 Stick (invention) | Example 13 Stick (not part of invention) |
|---|---|---|
| Polyethylene wax (Performalene 500-L Polyethylene - New Phase Technologies) | 4.1 | 4.1 |
| Ethylene Homopolymer (Performalene 400 Polyethylene - New Phase Technologies) | 8.3 | 8.3 |
| Cyclohexadimethylsiloxane (Dow Corning 246 Fluid - Dow Corning) | 26.4 | 26.4 |
| Phenyl Trimethicone (Dow Corning 556 Cosmetic Grade Fluid - Dow Corning) | 19.6 | 19.6 |
| Isohexadecane | 19.6 | 19.6 |
| Methyl Methacrylate Crosspolymer (Ganzpearl GMP 0820 - Ganz Chemical) | 15.0 | 15.0 |
| Sodium Polyacrylate (Luquasorb) | — | 6.5 |
| Expanded Milled Perlite (Optimat 1430 OR - World Minerals) | 6.5 | — |
| Micronized Zinc Pyrrolidone Carboxylate (UCIB - Solabia) | 0.5 | 0.5 |

Procedure:

The cyclopentasiloxane is heated to 65° C. The other ingredients are added (one by one) with the temperature remaining at 65-70° C. The whole (transparent solution) is homogenized for 15 minutes. The perlite or the superabsorbent polymer is added. The mixture is cooled to approximately 55° C. (a few ° C. above thickening of the mixture) and is cast in sticks. The resulting sticks are placed at 4° C. for 30 minutes.

Effectiveness Test

The stick containing the perlite was compared with the stick containing a superabsorbent, Luquasorb 1003, by 9 individuals. The test was carried out on 5 women and 4 men. Each product was applied to the armpits for 5 days, at a rate of one application per day.

For the men, the perlite stick was preferred since it does not form dry pellets under the arms, unlike the stick containing the Luquasorb 1003 superabsorbent. For the women, it is the perlite stick which emerges as the most effective. It appears that the stick containing the perlite is more effective or more cosmetic than that containing the superabsorbent.

Comparative Test of Antiperspirant Effectiveness Between a Perlite Stick and a Stick Containing Aluminium Chlorohydrate

| Ingredients (INCI name) | Example 14 Stick (invention) | Example 15 Stick (not part of invention) |
|---|---|---|
| Polyethylene wax (Performalene 500-L Polyethylene - New Phase Technologies) | 4.1 | 0 |
| Ethylene Homopolymer (Performalene 400 Polyethylene - New Phase Technologies) | 8.3 | 0 |
| Oxypropylenated butyl alcohol (Fluid AP, Low Odor - Amerchol Dow Chemical) | 0 | 10.0 |
| Isopropyl Palmitate | 28.5 | 12.5 |
| Stearyl alcohol (Lanette 18 - Cognis) | 0 | 15.0 |
| Hydrogenated castor oil (Cutina HR Pulver - Cognis) | 0 | 5.0 |
| Polyethylene Glycol Distearate (8 EO) (Dub DS PEG 8 - Stéarineries Dubois) | 0 | 2.5 |

-continued

| Ingredients (INCI name) | Example 14 Stick (invention) | Example 15 Stick (not part of invention) |
|---|---|---|
| Isohexadecane | 19.6 | 0 |
| Dicaprylyl Carbonate (Cetiol CC - Cognis) | 6.0 | 0 |
| N-Undecane/N-Tridecane mixture according to Example 1 or 2 of Document DE 10 2008 012 457 | 10.0 | 0 |
| Cyclopentadimethylsiloxane (Dow Corning 245 Fluid - Dow Corning) | 0 | 20.0 |
| Methyl Methacrylate Crosspolymer (Ganz Pearl GMP 0820 - Ganz Chemical) | 15.0 | 0 |
| Expanded Milled Perlite (Optimat 1430 OR - World Minerals) | 6.5 | 0 |
| Micronized Zinc Pyrrolidone Carboxylate (UCIB - Solabia) | 0.5 | 0.1 |
| Aluminium Chlorohydrate (Locron P - Clariant) | 0 | 20.0 |
| Fragrance | 1.5 | 1.5 |

The procedure is identical to that of Examples 12 and 13 above.

The in vivo effectiveness of the stick according to the invention was evaluated in comparison with a conventional aluminium chlorohydrate stick.

The test is carried out on a panel of 30 women between the ages of 18 and 50 who regularly (every day) use a fragranced, opaque white antiperspirant stick.

The following criteria were evaluated:

Effectiveness against wetness

Effectiveness against perspiration odours

Traces on clothing

Overall satisfaction.

The percentages of the women in favour, respectively, of the perlite-based stick 14 and those in favour of the aluminium salt-based stick 15 were measured. The results obtained are indicated in the following table:

| Criteria evaluated by 30 women | Stick No. 14 with perlite (invention) | Stick No. 15 with aluminium salt (not part of the invention) |
|---|---|---|
| Effectiveness against wetness | 87% | 47% |
| Effectiveness against perspiration odours | 90% | 77% |
| No trace on clothing | 80% | 60% |
| Overall satisfaction | 74% | 60% |

EXAMPLE 16

Anhydrous Cream

| Ingredients (INCI name) | Amounts as % by weight |
|---|---|
| Triethyl Citrate (Citroflex 2 - Reilly Chemicals) | 7.0 |
| Isopropyl Palmitate | 6.0 |
| Expanded Milled Perlite (Optimat 1430 OR - World Minerals) | 17.5 |
| Cyclopentadimethylsiloxane (Dow Corning 245 Fluid - Dow Corning) | 60.5 |
| Cyclopentasiloxane (and) Dimethiconol (Dow Corning 1501 Fluid (Dow Corning)) | 9.0 |

The Optimat® 1430 OR is dispersed in the mixture of the other starting materials by blade-mixing. A homogeneous paste is obtained.

EXAMPLE 17

Anhydrous Cream

| Ingredients (INCI name) | Amounts as % by weight |
|---|---|
| Isohexadecane | 18.5 |
| Hydrogenated Styrene/Isoprene Copolymer (Kraton G1701 E - Kraton Polymer) | 2.3 |
| Isononyl Isonanoate (Wickenol 151 - ALZO) | 22.5 |
| Petroleum Distillates (and) Disteardimonium Hectorite (and) Propylene Carbonate (Bentone Gel SS 71V - Elementis) | 16.1 |
| Expanded Milled Perlite (Optimat 1430 OR - World Minerals) | 20.0 |
| Cyclopentadimethylsiloxane (Dow Corning 245 Fluid - Dow Corning) | 20.6 |

Procedure:

The Optimat® 1430 OR is dispersed in the mixture of the other starting materials by blade-mixing. A homogeneous paste is obtained.

EXAMPLE 18

Aerosol

| Ingredients (INCI name) | Amounts as % by weight |
|---|---|
| Triethyl Citrate Citroflex 2 (Reilly Chemicals) | 1.0 |
| Stearalkonium Bentonite Tixogel MP 250 (Sud Chemie Rheolog.) | 0.2 |
| Isopropyl Palmitate | 0.9 |
| Expanded Milled Perlite (Optimat 1430 OR - World Minerals) | 2.6 |
| Cyclopentadimethylsiloxane (Dow Corning 245 Fluid - Dow Corning) | 9.0 |
| Cyclopentasiloxane (and) Dimethiconol (Dow Corning 1501 Fluid (Dow Corning)) | 1.3 |
| Isobutane (A-31 - Aeropres) | qs 100 |

Procedure:

The Optimat® 1430 OR is dispersed in the mixture of the other starting materials by blade-mixing, constituting phase A. This is pressurized in an aerosol container with isobutane.

EXAMPLE 19

Anhydrous Antiperspirant Stick

| Ingredients (INCI name) | Amounts as % by weight |
|---|---|
| Cyclopentadimethylsiloxane (Dow Corning 245 Fluid - Dow Corning) | 38.0 |
| PPG-14 Butyl Ether (Ucon Fluid AP - Amerchol) | 10.0 |
| Hydrogenated Castor Oil (Cutina HR - Cognis) | 4.0 |
| Stearyl Alcohol (Lorol $C_{18}$ - Cognis) | 14.0 |
| PEG-8 Distearate (Stearineries Dubois) | 2.0 |
| C12-15 Alkyl Benzoate Finsolv TN (Witco) | 15.0 |
| Expanded Milled Perlite (Optimat 1430 OR - World Minerals) | 17.0 |

Procedure:

The cyclopentasiloxane is heated to 65° C. The other ingredients are added (1 by 1) with the temperature remaining at 65-70° C. The whole is homogenized (transparent solution) for 15 minutes. The perlite is added. The mixture is cooled to approximately 55° C. (a few ° C. above thickening of the mixture) and cast in sticks. The resulting sticks are placed at 4° C. for 30 minutes.

EXAMPLE 20

Anhydrous Stick

| Ingredients (INCI name) | Amounts as % by weight |
|---|---|
| Polyethylene wax (Performalene 500-L Polyethylene - New Phase Technologies) | 6.2 |
| Ethylene Homopolymer (Performalene 400 Polyethylene - New Phase Technologies) | 26.7 |
| Isopropyl Palmitate | 15.0 |
| Isohexadecane | 19.6 |
| Dicaprylyl Carbonate (Cetiol CC - Cognis) | 6.0 |
| N-Undecane/N-Tridecane mixture according to Example 1 or 2 of Document DE10 2008 012 457 | 10.0 |
| Methyl Methacrylate Crosspolymer (Ganzpearl GMP 0820 - (Ganz Chemical) | 5.0 |
| Aluminium Chlorohydrate (Locron P - Clariant) | 10 |
| Expanded Milled Perlite (Optimat 1430 OR - World Minerals) | 6.5 |
| Micronized Zinc Pyrrolidone Carboxylate (UCIB (Solabia)) | 0.5 |
| Fragrance | 1.5 |

EXAMPLE 21

Anhydrous Stick

| Ingredients (INCI name) | Amounts as % by weight |
|---|---|
| Oxypropylenated Butyl Alcohol (Fluid AP, Low Odor - Amerchol - Dow Chemical) | 4.1 |
| Isopropyl Palmitate | 8.3 |
| Stearyl Alcohol | 28.5 |
| Hydrogenated Castor Oil (Cutina HR Pulver - Cognis) | 19.6 |
| Polyethylene Glycol Distearate (8 EO) (PEG 400 Distearate (DUB DS PEG 8) - Stearineries Dubois) | 6.5 |
| Cyclopentadimethylsiloxane (Dow Corning 245 Fluid - Dow Corning) | 21.0 |
| Aluminium Zirconium (73291) | 20.0 |
| Expanded Milled Perlite (Optimat 1430 OR - World Minerals) | 1.0 |
| Micronized Zinc Pyrrolidone Carboxylate (UCIB (Solabia)) | 0.1 |
| 1159 M | 0.5 |

EXAMPLE 22

Water-in-Oil Emulsion Stick

| Ingredients (INCI name) | Amounts as % by weight | Phase |
|---|---|---|
| Ethylene Homopolymer (Performalene 400 Polyethylene - New Phase Technologies) | 9.0 | A |
| Beneth-10 (Eumulgin BA 10 - Cognis) | 2.0 | |
| Cetyl PEG/PPG-10/1 Dimethicone (Abil EM 90 - Goldschmidt) | 2.0 | |
| Polyglyceryl-3 Diisostearate (Lameform TGI - Cognis) | 0.3 | |
| Isopropyl Palmitate | 9.0 | |
| Cyclopentadimethylsiloxane (Dow Corning 245 Fluid - Dow Corning) | 6.0 | |
| Cyclopentasiloxane (and) PEG/PPG-18/18 Dimethicone (Dow Corning 5225C Formulation Aid - Dow Corning) | 2.0 | |
| PEG-14M (Polyox WSR 205 - Amerchol) | 0.5 | B |
| Magnesium Sulphate | 1.0 | |
| Glycerol | 1.0 | |
| Aluminium Chlorohydrate Chlorhydrol (Aluminium Chlorohydrate 50% W/W Solution - Reheis) | 40.0 | |
| Expanded Milled Perlite (Optimat 1430 OR - World Minerals) | 1.0 | |
| Preservatives | qs | B3 |
| Water | qs 100 | qs 100 |

Procedure

Phase A and phase B are introduced. The mixture is heated at 90° C. until homogenization, and sufficient stirring is performed if necessary. Phase B3 is added at 90° C. This phase may contain preservatives, active agents or other starting materials that are temperature-sensitive and that it is preferable not to heat for too long. The mixture is heated to 95° C. so as to be able to cast sticks at 91-92° C.

The invention claimed is:

1. A cosmetic method for reducing human perspiration and, optionally, human body odours, on skin which comprises applying, to a surface of human skin in need thereof, an antiperspirant composition comprising an effective amount of expanded amorphous milled perlite particles having a particle size defined by a median diameter $D_{50}$ ranging from 0.5 to 50 μm; at least one antiperspirant salt or complex is chosen from aluminum salts or complexes and/or zirconium salts or complexes; and a cosmetically acceptable carrier and wherein the composition is in the form of a stick or is applied to the skin using an aerosol device, a pump dispenser or roll-on applicator, or in the form of a loose or compacted powder or packaged in a device fitted with a perforated wall;

and then permitting said composition to dry on said surface or when applied as a loose or compacted powder, the expanded amorphous milled perlite particles are thereby available for reducing the human perspiration.

2. The method according to claim 1, in which the expanded amorphous milled perlite particles are obtained by thermal expansion of a volcanic rock comprising from 1% to 10% by weight of water, and less than 10% by weight of crystalline rock, relative to the total weight of the composition of the rock, followed by milling.

3. The method according to claim 1, in which the composition also comprises at least one deodorant active agent.

4. The method according to claim 1, in which the at least one antiperspirant salt or complex is chosen from aluminum halohydrates; aluminum zirconium halohydrates, and complexes of zirconium hydroxychloride and of aluminum hydroxychloride with or without an amino acid.

5. The method according to claim 2, wherein the amount of water is from 1% to 5% by weight relative to the total weight of the composition of the rock.

6. The method according to claim 1, wherein the expanded amorphous milled perlite particles have a particle size defined by a median diameter $D_{50}$ ranging from 0.5 to 40 μm.

7. The method according to claim 1, wherein the amount of the expanded amorphous milled perlite particles used is from 5% to 60%, by weight of the total weight of the composition.

8. The method according to claim 1, which comprises applying said composition containing said expanded amorphous milled perlite particles to skin on underarms of the human.

9. The method according to claim 1, wherein the composition is in the form of a stick or is applied to the skin using an aerosol device, a pump dispenser or roll-on applicator.

10. The method according to claim 1, wherein the expanded amorphous milled perlite particles have a platelet shape.

11. The method according to claim 1, wherein the composition is applied to the skin using an aerosol device, wherein said composition is pressurized in the aerosol device, wherein a propellant chosen from the group of dimethyl ether, optionally substituted with at least one compound chosen from the group of monofluorotrichloromethane, ditluorodichloromethane, tetrafluorodichloroethane and 1,1 difluoroethane; carbon dioxide, nitrous oxide, nitrogen and pressurized air; and wherein the propellant is present in a pressurized concentration of 50% to 85% by weight of the total weight of the pressurized composition.

12. The method according to claim 1, wherein the composition is applied to the skin using an aerosol device, wherein said composition is pressurized in the aerosol device, and wherein isobutane is present in a pressurized concentration of 50% to 85% by weight of the total weight of the pressurized composition.

13. The method according to claim 1, wherein the composition further comprises at least one suspension agent chosen from the group of reaction product of bentonite with quaternary ammonium stearalkonium chloride and reaction product of hectorite with distearyldimonium chloride in an amount of 0.2% to 2% by weight relative to the total weight of the composition.

14. The method according to claim 1, wherein the at least one antiperspirant salt or complex is chosen from aluminium chlorohydrex, aluminium chlorohydrex polyethylene glycol complex, aluminium chlorohydrex propylene glycol complex, aluminium dichlorohydrate, aluminium dichlorohydrex 5 polyethylene glycol complex, aluminium dichlorohydrex propylene glycol complex, aluminium sesquichlorohydrate, aluminium sesquichlorohydrex polyethylene glycol complex, aluminium sesquichlorohydrex propylene glycol complex, and 10 aluminium sulphate buffered with sodium aluminium lactate.

15. The method according to claim 1, wherein the at least one antiperspirant salt or complex is chosen from aluminium zirconium octachlorohydrate, aluminium zirconium pentachloro-15 hydrate, aluminium zirconium tetrachlorohydrate and aluminium zirconium trichlorohydrate.

16. The method according to claim 1, wherein the at least one antiperspirant salt or complex is chosen from aluminium zirconium octachlorohydrex glycine, aluminium zirconium pentachlorohydrex glycine, aluminium zirconium tetrachlorohydrex glycine and aluminium zirconium trichlorohydrex glycine complexes.

17. The method according to claim 1, wherein the at least one antiperspirant salt or complex comprises aluminium chlorohydrate.

18. The method according to claim 17, wherein the amount of the aluminium chlorohydrate is 0.5% to 25% by weight relative to the total weight of the composition.

19. The method according to claim 17, wherein the amount of the at least one antiperspirant salt or complex is 0.5% to 25% by weight relative to the total weight of the composition.

20. The method according to claim 1, wherein the expanded amorphous milled perlite particles have a platelet shape and wherein the composition further comprises at least one suspension agent chosen from the group of reaction product of bentonite with quaternary ammonium stearalkonium chloride and reaction product of hectorite with distearydimonium chloride in an amount of 0.2% to 2% by weight relative to the total weight of the composition.

* * * * *